United States Patent [19]
Hohn

[11] Patent Number: 5,147,318
[45] Date of Patent: Sep. 15, 1992

[54] VALVED ARTERIAL CATHETER

[75] Inventor: David C. Hohn, Houston

[73] Assignee: Board of Regents, The University of Texas System, Houston, Tex.

[21] Appl. No.: 664,362

[22] Filed: Mar. 4, 1991

[51] Int. Cl.$^5$ .............................................. A61M 5/32
[52] U.S. Cl. ................................... 604/174; 604/247; 604/280
[58] Field of Search ............. 604/264, 272, 174, 175, 604/280, 281, 282, 247, 43, 283

[56] References Cited

U.S. PATENT DOCUMENTS

| | | | |
|---|---|---|---|
| 2,969,066 | 1/1961 | Holter et al. | 128/350 |
| 3,020,913 | 2/1962 | Heyer | 128/350 |
| 3,228,894 | 1/1966 | Jeckel | 604/280 X |
| 3,885,561 | 5/1975 | Cami | 128/214 |
| 3,888,249 | 6/1975 | Spencer | 128/214 R |
| 4,190,909 | 3/1980 | Ablaza | 3/1.4 |
| 4,434,810 | 3/1984 | Atkinson | 137/493 |
| 4,657,536 | 4/1987 | Dorman | 604/247 |
| 4,685,905 | 8/1987 | Jeanneret nee Aab | 604/247 |
| 4,701,166 | 10/1987 | Groshong et al. | 604/247 |
| 4,784,646 | 11/1988 | Feingold | 604/175 |
| 4,801,297 | 1/1989 | Mueller | 604/280 |
| 5,030,210 | 7/1991 | Alchas | 604/247 |

FOREIGN PATENT DOCUMENTS 8303535 10/1983 World Int. Prop. O. ............ 604/43

Primary Examiner—John D. Yasko
Attorney, Agent, or Firm—Wolf, Greenfield & Sacks

[57] ABSTRACT

A catheter for arterial delivery of medication or the like includes an elongate flexible shaft with a self-sealing valve element at the distal tip of the shaft. The tip is molded from polymeric material filled with a radiopaque compound and is visually dark to facilitate surgical implantation. The value element also includes a pair of closely spaced circumferential retention ridges to facilitate securing the device in an artery by sutures or the like. Retention ridges are located very close to each other to reduce the risk of axial shifting of the device in the artery and are located close to the distal tip of the tip element to reduce the formation of spaces in which thrombus might develop.

14 Claims, 1 Drawing Sheet

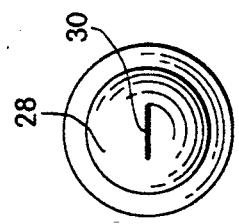
Fig. 1
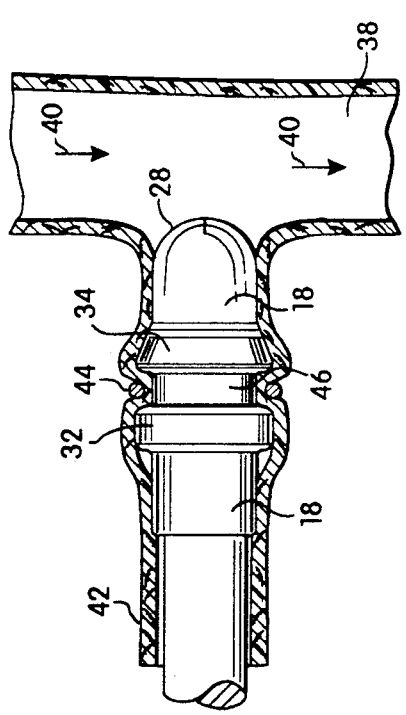
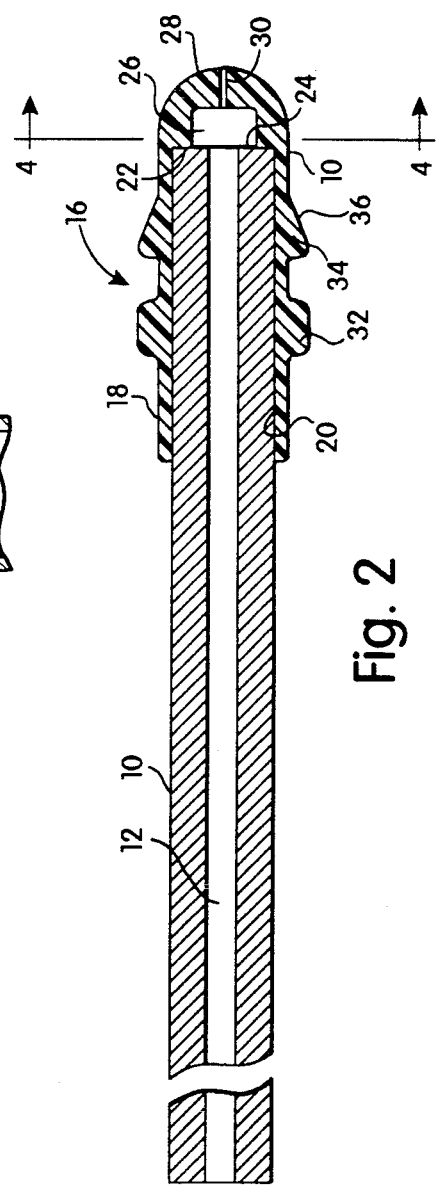
Fig. 2
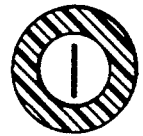
Fig. 4

VALVED ARTERIAL CATHETER

FIELD OF THE INVENTION

This invention relates to catheters for arterial delivery of medication.

BACKGROUND OF THE INVENTION

It is a common medical practice to deliver medication to a patient by direct delivery of that medication into a blood vessel. Typically, intravenous delivery of the medication is employed when it is desired to deliver the medication systemically, that is, throughout the patient's body. When delivered intravenously, the medication returns through the venous system to the heart from which it is then pumped throughout the patient's arterial system to all parts of the patient's body. When it is desired to deliver medication to a specific, targeted organ, or to another localized portion of the patient's anatomy, the medication may be delivered into a specific artery leading to that organ or region. Medicine delivered through an artery is transported only to the organ or region to which the artery leads and not throughout the body. For example, it is a common practice when treating a malignancy of the liver with chemotherapy to deliver the medication through a catheter inserted into the hepatic artery which leads directly to the liver. The catheter may be connected to a subcutaneous port that is accessible by needle puncture through the skin or may be implanted in a manner such that its proximal end protrudes through the patient's skin for direct connection to a syringe or other medication injection device.

Delivery of medication through a patient's arteries presents considerations not present in venous delivery. For example, the blood pressure in the arterial system is considerably higher than in the venous system. Consequently, catheters used to deliver medication to an artery typically must have a thicker wall to reduce the chance of the catheter rupturing under the influence of the increased arterial pressure. Additionally, arterial blood has an increased tendency for retrograde flow into the catheter leading to thrombotic occlusion. Because of the increased blood pressure in the arterial system, it is important that the outlet of the catheter have a valve arrangement to prevent backflow of blood into the catheter.

Still another factor that must be considered is the manner in which the catheter will be held in place in the arterial system. It is important that the catheter be securely held so that it does not shift about to different positions. Such shifting could result in the catheter partially obstructing blood flow through the artery which would tend to create turbulence and increase the risk of clotting. Typically, such catheters are placed in a branch artery leading to the artery to which the medication is to be delivered. Thus, the outlet of the catheter is located at the juncture of the catheterized artery and the artery to which the medication is to be delivered. If the catheter is permitted to shift its position longitudinally in the branch artery, its outlet tip may project excessively into the artery to be medicated, partially obstructing that artery and increasing turbulence.

It would be desirable and there is a need to provide a valved catheter for arterial delivery of medication that reduces the tendency to clot and which effectively achieves the foregoing and other objectives.

SUMMARY OF THE INVENTION

In accordance with the invention, a catheter is provided and includes an elongate flexible shaft with a valve element mounted on the end of the shaft that is to be inserted into the patient's artery (the distal end). The tip element is molded from a polymeric material, preferably filled with a radiopaque compound so that its position may be monitored fluoroscopically after the catheter is implanted. The valve tip includes a hemispherical distal surface having a normally closed transverse slit. The more proximal portion of the valve element includes a pair of closely spaced circumferential retention ridges including a proximal ridge and a distal ridge. The distal ridge preferably has a beveled surface facing the distal direction to reduce the trauma of insertion of the device into the patient. The catheter is implanted surgically by inserting it into a branch artery of the main artery into which the medication is to be infused. The catheter is advanced along that branch artery until the distal tip is at the entrance to the main artery but in a manner such that the distal tip does not protrude significantly into that artery. The polymeric material from which the valve element is formed is visually dark so that the position of the tip element can be seen through the translucent artery wall during the insertion procedure. Once the catheter tip is properly positioned, it is secured in place by sutures tied about the artery between the retention ridges. The retention ridges are located very close to each other so that the amount of possible axial shifting of the catheter in the branch vessel is minimized, thereby reducing the risk of the catheter tip projecting too far into the main artery. Additionally, the retention ridges are located in close proximity to the distal tip of the tip element to avoid creation of a relatively large dead space around the catheter tip in which thrombus might accumulate.

It is among the general objects of the invention to provide an improved valved arterial catheter.

Another object of the invention is to provide a valved arterial catheter which reduces the tendency of clotting within the artery.

A further object of the invention is to provide a valved arterial catheter that can be secured in an artery in a manner so that it does not shift position within the artery.

Another object of the invention is to provide a valved arterial catheter having an improved valve arrangement at its distal end.

Still another object of the invention is to provide a valved arterial catheter in which the valve at the distal end opens under a controlled low pressure, yet which presents significant resistance to opening under the back pressure of the arterial blood.

A further object of the invention is to provide an improved valved arterial catheter that displays reduced trauma to the artery when inserted into the artery.

Another object of the invention is to provide a valved arterial catheter having means to facilitate proper and precise location and orientation of the catheter in the patient's arteries.

DESCRIPTION OF THE DRAWINGS

The foregoing and other objects and advantages of the invention will be appreciated more fully from the following further description, with reference to the accompanying drawings in which:

FIG. 1 is an illustration of the juncture of two arteries in which the catheter embodying the invention has been placed in one of the arteries so that its tip is located in proximity to the juncture, with the valved outlet being placed so as not to protrude significantly into the artery into which the medication is to be delivered;

FIG. 2 is a longitudinal, sectional, fragmented illustration of the catheter, including the catheter tip, in accordance with the invention;

FIG. 3 is an end view of the distal end of the catheter tip as seen from the right of FIG. 2; and FIG. 4 is a sectional illustration taken through the catheter tip as seen along the line 4—4 of FIG. 2.

DESCRIPTION OF THE PREFERRED EMBODIMENT

FIG. 2 illustrates the catheter in longitudinal section. The catheter includes an elongate flexible tubular shaft 10 which may be formed from an appropriate polymeric material. For example, the shaft may be formed from silicone rubber. Its length and diameter may be varied to suit the specific procedure with which the catheter is to be used. By way of example, the catheter shaft may have an outer diameter of the order of 0.080". It may be provided in a length of the order of 50 cm but may be trimmed to length adapted for the specific implantation. The shaft 10 has a single lumen 12 extending the length of the shaft. The wall thickness of the shaft 10 may be relatively thick, at least sufficiently thick for the material from which it is made so that it will safely resist collapse under the influence of arterial blood pressure and also so that it may be tunneled across the abdomen. For example, the wall thickness may be of the order of 0.030". The proximal end of the catheter (to the left in FIG. 2) may terminate as shown without any fitting so that it may be connected to the outlet of a subcutaneously implantable port. By way of example, such ports are illustrated in U.S. Pat. Nos. 4,915,690 and 4,900,312. to which reference is made. Such ports, subcutaneously implanted, are connected to the proximal end of the catheter to deliver medication from the port through the catheter. The catheter, in such an application, is fully implanted beneath the patient's skin. In some applications, it may be preferable to cause the catheter to exit from the patient's skin to be connectable to a pressure infusion pump or other means for delivering medication through the catheter.

The distal end of the catheter includes a valve tip element, indicated generally at 16. The valve tip 16 preferably is molded from an appropriate polymeric material such as liquid silicone rubber. Preferably, the silicone rubber material is filled with a visually dark radiopaque material such as powdered tungsten so that once implanted in the patient, the position of the catheter tip may be monitored under fluoroscopic x-ray. Additionally, the dark appearance of valve tip 16 facilitates its placement, as will be described. Preferably the tungsten powder is mixed with the liquid silicone rubber so that it is proportionally about 33% tungsten powder, by weight. The valve tip 16 includes a generally cylindrical body 18 that defines a proximally-facing socket 20 that receives the distal end of the catheter shaft 10. The bore 20 terminates, at its inner, distal end in a shoulder 22 against which the distal surface 24 of the catheter shaft seats. A smaller diameter chamber 26 is formed in the valve tip 16 distally of the shoulder 22. The distal end of the valve tip is formed to define a hemispherical distal surface 28. A transversely extending slit 30 is formed in the hemispherical end of the valve tip 16. The more proximal portions of the valve tip include a pair of closely-spaced annular retention ridges including a proximal ridge 32 and a distal ridge 34. The distal ridge 34 preferably is formed with a distally-facing beveled surface 36.

The valve tip 16 is molded directly onto the distal end of the catheter shaft in an insert molding procedure and also is formed from silicone rubber material so that it will bond to the catheter shaft under the influence of heat and pressure of the molding procedure. Before molding the tip onto the end of the catheter shaft, a pin insert is placed in the bore of the distal end of the shaft. The pin insert includes a head which will form the chamber 26 in the tip. The head and pin resemble somewhat the head end of a nail. The pin provides support for the catheter shaft during the molding procedure and also defines the chamber 26. The thickness of the head determines the depth of the chamber 26 and, therefore, the thickness of the distal hemispherical portion of the tip. The thickness of that portion of the tip affects the resilient and flexing characteristics of the valve element defined by the slit 30. Additionally, the use of the headed pin facilitates formation of the slit and that the head provides a firm surface against which the slit 30 may be made. After the slit is made, the headed pin is withdrawn from the assembly through the slit.

By way of dimensional example, the tip may be of the order of 0.3" long. The outer diameter defined by the ridges may be of the order of 0.13". The ridges may each be approximately 0.40" wide and, preferably, spaced close to each other so that the space between the ridges 32, 34 is of the order of 0.035" in width. The beveled surface 36 of the distal ridge 34 may be inclined at an angle of approximately 30° to the axis of the catheter. The distal end of the distal ridge 34 may be spaced from the hemispherical distal tip of the order of 0.10". The depth of the chamber 26 may be of the order of 0.03".

FIG. 1 illustrates somewhat diagrammatically, the manner in which the distal tip of the catheter is intended to be located and secured in position in the patient's arteries. FIG. 1 shows a branch of two arteries including a delivery artery 38 through which blood flows in the direction indicated by the arrow 40. The delivery artery 38 leads to a specific targeted organ or other region of the patient's anatomy to which medication is to be delivered. In order to deliver the medication to the delivery artery 38, the catheter of the present invention is inserted into a branch artery 42 in the region of the juncture between the branch artery 42 and the delivery artery 38. As shown in FIG. 1, the distal end of the catheter is located in the region of the juncture so that the valve tip 16 is disposed, preferably as shown, with the hemispherical tip 28 exposed to the lumen of the delivery artery 38, but not protruding appreciably into the delivery artery 38. Once the catheter is positioned with its tip in that location, the tip of the catheter is further secured in place by tying sutures, indicated generally at 44, about the exterior of the branch artery 42 in the region of the annular groove 46 defined between the proximal and distal retention ridges 32, 34. By locating the retention ridges 32, 34 close to each other, the width of the annular groove 46 is maintained at a minimum so that the sutures 44 will constrict an annular region of the wall of the branch artery 42 within the annular groove 46, substantially occupying the annular groove 46. So retained, the tip 16 is unable to shift axially within the branch artery and, therefore, the hemispherical tip 28 will remain in place and will not protrude into the delivery artery 38.

The catheter is implanted in a surgical procedure in which the branch regions of the branch artery 42 and the delivery artery 38 are surgically exposed. The physician in a typical procedure, will excise a segment of the branch artery, thus sacrificing that artery. The distal end of the catheter then is inserted into the stub end of the branch artery. Once in the branch artery, the catheter is advanced. The beveled distally-facing, leading surface of the distal retention ridge 34 serves to progressively dilate the artery and reduce the insection trauma by providing a wedge-like advancing member to the artery. The precise location of the location of the tip of the artery may be determined by visual inspection at the region of the juncture of the arteries 42, 38. Typically, the wall of the artery 42 has some translucency through which the position of the visually dark tip 16 may be discerned. Thus, the catheter may be advanced to the precise position intended and, once in that position, the sutures 44 are tied about the artery to constrict the arterial wall within the annular groove 46, thereby securing the catheter in place. The proximal end of the catheter then may be connected to the subcutaneous port or may be tunneled to an exposure site where it may be exposed through the patient's skin for connection to an external infusion pump or the like.

Preferably, the retention ridges are located close to the catheter tip so as to avoid creation of relatively long "dead space" within the branch artery in which blood might accumulate and develop into clots. Should it be desired to inspect the location of the catheter tip, that may be accomplished with x-ray fluoroscopy. The radiopaque quality of the tip 16 enables the catheter tip to be so visualized.

The tip preferably is designed so that it will open under relatively low pressures yet will self-seal completely to prevent blood from backflowing through the valve. Preferably the thickness of the silicone rubber at the hemispherical tip end, in the region of the slit is such that the slit valve will open at pressures less than about 10 psi injection pressure and, preferably, will open at pressures of the order of 3 to 4 psi. Preferably, the valve should maintain flow rates of the order of 4 ml per minute at a pressure of about 10 psi.

From the foregoing, it will be appreciated that the invention provides a simple, easily manufactured yet effective valved arterial catheter which minimizes dead spaces and clotting, can be secured in the artery so as to reduce the chance of shifting its position, opens under a controlled low pressure yet provides significant resistance to opening of the valve under the influence of arterial pressure, provides for reduced insertion trauma and provides means for visually facilitating placement and subsequent fluoroscopic examination of the position of the catheter.

It should be understood, however, that the foregoing description of the invention is intended merely to be illustrative thereof and that other embodiments, modifications and equivalents may be apparent to those skilled in the art without departing from its spirit.

Having thus described the invention, what we desire to claim and secure by Letters Patent is:

1. An arterial valved catheter for arterial delivery of medication comprising:
    an elongate flexible tubular shaft having a lumen extending therethrough;
    a tip mounted on and closing off the distal end of the shaft, the tip having a self-sealing slit formed at its distal end and in communication with the lumen; and
    a pair of annular retention ridges formed on the exterior of the tip in close proximity to each other and in proximity to the distal end of the tip, the ridges being defined by radially extending circumferential flanges on opposite sides of and defining a groove therebetween whereby the device may be secured in position in an artery by securing a constricting member about the artery in the region of the groove to constrict the artery tightly about the catheter tip in the region of the groove.

2. The catheter as defined in claim 1 wherein the distally-facing surface of the distal ridge is beveled.

3. The catheter as defined in either of claims 1 or 2 wherein the tip is visually dark as compared to the more proximal portions of the catheter.

4. The catheter as defined in claims 1 or 2 wherein the tip is formed from a material including radiopaque elements.

5. The catheter as defined in claim 1 wherein the distal end of the valve tip is hemispherical and is polished substantially smooth.

6. A catheter as defined in any one of claims 1, 2 or 5 in which the shaft and the tip are formed from silicone rubber.

7. A catheter as defined in claim 3 wherein the shaft and the tip are formed from silicone rubber.

8. A catheter as defined in claim 4 wherein the shaft and the tip are formed from silicone rubber.

9. A catheter as defined in claim 8 wherein the radiopaque element comprises a powdered filler formed from radiopaque material incorporated into the silicone rubber of the tip so as to render the tip visually dark as compared to the more proximal portions of the catheter.

10. A catheter as defined in claim 9 wherein the powdered radiopaque material comprises powdered tungsten.

11. A catheter as defined in claim 10 wherein the powdered tungsten is incorporated into the silicone rubber of the tip in a proportion of 33% by weight.

12. A catheter as defined in claim 1 further comprising:
    the tip having a chamber formed in the region between the distal tip of the catheter shaft and the self sealing slit.

13. An arterial valved catheter as defined in any one of claims 1, 2 or 5 wherein the self-sealing slit comprises a single slit and being the sole self-sealing slit of the tip.

14. An arterial valved catheter as defined in any one of claims 1, 2 or 5 wherein said self-sealing slit is constructed to enable one-way flow of liquid from the catheter into the patient.

* * * * *